United States Patent
Hähnle et al.

(10) Patent No.: US 6,828,354 B2
(45) Date of Patent: Dec. 7, 2004

(54) HYDROPHILIC OPEN-CELL, ELASTIC FOAMS WITH A MELAMINE/FORMALDEHYDE RESIN BASE, PRODUCTION THEREOF AND USE THEREOF IN HYGIENE PRODUCTS

(75) Inventors: Hans-Joachim Hähnle, Neustadt (DE); Horst Baumgartl, Ludwigshafen (DE); Norbert Herfert, Altenstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 101 days.

(21) Appl. No.: 10/380,481

(22) PCT Filed: Sep. 19, 2001

(86) PCT No.: PCT/EP01/10846

§ 371 (c)(1),
(2), (4) Date: Mar. 10, 2003

(87) PCT Pub. No.: WO02/26872

PCT Pub. Date: Apr. 4, 2002

(65) Prior Publication Data

US 2004/0039074 A1 Feb. 26, 2004

(30) Foreign Application Priority Data

Sep. 27, 2000 (DE) .......................................... 100 47 719

(51) Int. Cl.[7] .............................. C08J 9/00; A61F 13/15; A61F 13/20
(52) U.S. Cl. ......................... 521/187; 521/188; 521/64; 604/359; 604/368
(58) Field of Search ........................... 521/64, 187, 188; 604/359, 368

(56) References Cited

U.S. PATENT DOCUMENTS

| | | |
|---|---|---|
| 4,332,937 A | 6/1982 | Zink |
| 4,334,971 A | 6/1982 | Mahnke et al. |
| 4,511,678 A | 4/1985 | Mahnke et al. |
| 4,540,717 A | 9/1985 | Mahnke et al. |
| 5,318,554 A | 6/1994 | Young et al. |
| 5,550,167 A | 8/1996 | DesMarais |

FOREIGN PATENT DOCUMENTS

| | | |
|---|---|---|
| DE | 100 27 770 | 12/2001 |
| DE | 100 34 505 | 2/2002 |
| EP | 0 017 621 | 12/1982 |
| EP | 0 017 672 | 4/1983 |
| EP | 0 037 470 | 6/1985 |
| GB | 1 570 485 | 7/1980 |
| WO | WO 96/21682 | 7/1996 |
| WO | WO 97/07832 | 3/1997 |

*Primary Examiner*—Morton Foelak
(74) *Attorney, Agent, or Firm*—Marshall, Gerstein & Borun LLP

(57) ABSTRACT

Hydrophilic open-celled resilient foams comprising melamine-formaldehyde resins, obtainable by (a) heating and crosslinking an aqueous solution or dispersion each containing at least a melamine-formaldehyde precondensate, an emulsifier, a blowing agent and a curing agent to form a foam, (b) then conditioning the foam at from 120 to 300° C. for from 1 to 180 minutes to remove volatiles, and (c) treating the foam during the conditioning or thereafter with at least one polymer containing primary and/or secondary amino groups and having a molar mass of not less than 300, are useful in hygiene articles to acquire, distribute and immobilize body fluids.

18 Claims, No Drawings

HYDROPHILIC OPEN-CELL, ELASTIC FOAMS WITH A MELAMINE/FORMALDEHYDE RESIN BASE, PRODUCTION THEREOF AND USE THEREOF IN HYGIENE PRODUCTS

CROSS REFERENCE TO RELATED APPLICATION

This is the U.S. national phase application of International Application No. PCT/EP01/10846, filed Sep. 19, 2001.

The present invention relates to hydrophilic open-celled resilient foams based on melamine-formaldehyde resins, their preparation and their use in hygiene articles.

EP-A-0 017 621 and EP-A-0 017 672 disclose open-celled resilient foams based on melamine-formaldehyde condensation products and to processes for their preparation. The process known from EP-A-0 037 470 produces open-celled resilient foams from melamine-formaldehyde condensation products in a particularly advantageous manner by reaction of microwave energy (ultra high frequency irradiation) on an aqueous solution or dispersion containing in each case a melamine-formaldehyde precondensate, an emulsifier, a blowing agent and a curing agent. The solution or dispersion is heated in such a way that it foams up and cures the precondensate. The foams thus obtainable emit small amounts of formaldehyde at a rate which increases with increasing foam temperature and moisture content.

The construction of hygiene articles and use of open-celled foams of melamine-formaldehyde resins as adsorbent interlayer is extensively described in prior DE application No. 100 34 505.0, unpublished at the priority date of the present invention. The melamine-formaldehyde resin foams recited therein are highly hydrophilic, but they give off a comparatively large amount of formaldehyde on contact with body fluids. This substantially limits the possibility of using such foams in hygiene articles.

Prior DE application No. 100 27 770.5, unpublished at the priority date of the present invention, describes the preparation of foams from low-formaldehyde open-celled melamine-formaldehyde resins having a molar ratio of melamine to formaldehyde in the range from 1:1.0 to 1:1.9. These foams emit less than 30 mg of formaldehyde per kg of foam even under the warm-moist conditions customary in the hygiene sector (EU Standard EN ISO 14 184-1, water immersion at 40° C. for 1 h). They consequently meet the baby clothing requirements of Oeko-Tex Standard 100 (quality mark of textiles tested for harmful substances). However, the appreciable reduction in formaldehyde emission comes at the expense of a partial loss of hydrophilic properties of the foam, as a result of which the liquid acquisition rate of such foam layers decreases.

WO-A-96/21682 discloses foams which, owing to their open-celled structure with relatively large openings and channels, are very useful for absorbing aqueous body fluids, especially blood. The foams are obtained by polymerization of ($C_4$–$C_{14}$)alkyl acrylates, ($C_6$–$C_{16}$)alkyl methacrylates, ($C_4$–$C_{12}$)alkyl-styrenes as monomers, preferably styrene and ethyl-styrene as comonomers, also aromatic polyvinyl compounds as crosslinkers; optionally polyfunctional acrylates, methacrylates, acrylamides and methacryl-amides and mixtures thereof as additional crosslinker substances. The polymerization takes place within a High Internal Phase Emulsion (HIPE) of the W/O type in which the weight ratio of water phase to oil phase is in the range from 20:1 to 125:1. After the polymerization has ended, the polymer foams are washed and dried.

WO-A-97/07832, U.S. Pat. No. 5,318,554 and U.S. Pat. No. 5,550,167 concern the production of open-celled foams based on HIPE emulsions and their use for absorbing aqueous body fluids. However, the open-celled foams are always used together with other components responsible for the ultimate absorption (immobilization) of the body fluids. The materials have good application advantages, but also clear in the hygiene article disadvantages.

For instance, the production of these materials is an extremely complicated process which is difficult to control. The enormous amount of aqueous phase (aqueous salt solution) required is neither economically nor ecologically sensible. Moreover, the materials are hydrophilicized at the surface with a salt layer. This layer can become detached during use and pass into the storage medium of the absorbent core. The storage medium is generally made of superabsorbents. It is known that superabsorbents are susceptible to "salt poisoning," i.e., their absorbency decreases dramatically with the increasing salt content of the solution to be absorbed. It can, therefore, certainly not be desirable to additionally increase the salt load in the body fluids to be absorbed.

It is an object of the present invention to provide open-celled resilient foams based on melamine-formaldehyde resins that are hydrophilic and whose formaldehyde emissions are substantially reduced compared to existing foams of melamine-formaldehyde resins.

We have found that this object is achieved by hydrophilic open-celled resilient foams comprising melamine-formaldehyde resins, obtainable by (a) heating and crosslinking an aqueous solution or dispersion each containing at least a melamine-formaldehyde precondensate, an emulsifier, a blowing agent and a curing agent to form a foam, (b) then conditioning the foam at from 120° C. to 300° C. for from 1 to 180 minutes to remove volatiles, and (c) treating the foam during the conditioning or thereafter with at least one polymer containing primary and/or secondary amino groups and having a molar mass of not less than 300.

The foams are prepared using, for example, melamine-formaldehyde precondensates where the molar ratio of melamine to formaldehyde is in the range from 1:1.0 to 1:5.0. Preference was given to melamine-formaldehyde precondensates where the molar ratio of melamine to formaldehyde is in the range from 1:2.0 to 1:5.0, especially in the range from 1:2.5 to 1:3.5. The molar mass of the polymers which contain primary and/or secondary amino groups and are present as modifiers on the hydrophilic open-celled resilient foams is, for example, in the range from 500 to 5 million, preferably in the range from 1,000 to 100,000. These foams preferably include vinylamine polymers, polyethyleneimines, polyallylamines, lysine condensates or mixtures thereof to reduce formaldehyde emissions with or without hydrophilic properties being imparted.

Such foams have, for example, a density of from 5 to 200 g/l, a specific surface area (determined according to BET) of more than 0.5 $m^2$/g and a Free Swell Capacity of more than 20 g/g. They have, for example, in the wet state a tensile strength of >60 $J/m^2$.

The invention also provides a process for preparing hydrophilic open-celled resilient foams comprising melamine-formaldehyde resins, which comprises (a) heating and crosslinking an aqueous solution or dispersion each containing at least a melamine-formaldehyde precondensate, an emulsifier, a blowing agent and a curing agent to form a foam, (b) then conditioning the foam at from 120° C. to 300° C. for from 1 to 180 minutes to remove volatiles, and (c) treating the foam during the conditioning or thereafter with at least one polymer containing primary and/or secondary amino groups and having a molar mass of not less than 300.

Process steps (a) and (b) are known from the prior art, cf. the above-discussed references EP-A-0 017 621, EP-A-0 017 672 and EP-A-0 037 470. The foaming as per step (a) is effected by heating the mixture to a temperature above the boiling point of the blowing agent and is carried out, for example, in such a way that initially there is little increase in the viscosing and a steep rise in the viscosity and crosslinking substantially does not occur until the foaming process has ended. However, foaming of the mixture and crosslinking of the precondensate may also be effected concurrently. Heating of the mixture is effected, for example, using hot air, steam and/or by utilizing heat of reaction. The foaming of the aqueous mixture of melamine-formaldehyde precondensate, emulsifier, blowing agent and curing agent is preferably effected by means of microwaves according to the process known from EP-A-0 0 37 470.

Structure and mechanical properties of the foams are known from and EP-A-0 017 672:

- the DIN 53 420 density is in the range from 1.6 to 30, preferably from 2 to 20 [g/l];
- the DIN 52 612 coefficient of thermal conductivity is less than 0.06, preferably less than 0.04 [W.m-1K-1];
- the DIN 53 577 compression hardness on 60% compression, divided by the density, is less than 0.3, preferably less than 0.2 [N.cm$^2$/g.l-1], the determination of the compression hardness at 60% compression having to be followed by a recovery of the foam to at least 70%, preferably at least 90%, especially 95%, of its original dimensions;
- the modulus of elasticity on the lines of DIN 53 423, divided by the density, is less than 0.25, preferably less than 0.15 [N.mm-2/g.l-1];
- the DIN 53 423 bending travel on fraction is more than 10, preferably more than 15 [mm];
- the DIN 53 527 compression set on 50% compression is less than 45%, preferably less than 30%, especially less than 10%;
- the DIN 18 165 dynamic stiffness for a sheet thickness of 50 mm is less than 20, preferably less than 10, especially less than 5 [N.cm-3];
- under DIN 4102 they have at most normal flammability, preferably low flammability;
- tensile strength in the wet state >60 J/m$^2$;
- BET surface area of foam >0.5 m$^2$/g.

The foams which are based on melamine-formaldehyde condensation products and which are used according to the invention are open-celled. Under the microscope, the foam structure is seen to contain a multiplicity of interconnected, three-dimensionally branched webs. Melamine-formaldehyde resin foams are sufficiently resilient only, for example, when the webs meet the conditions described in EP-A-0 017 672, i.e., the average ratio of web length to web thickness is greater than 10:1, preferably greater than 12:1, especially greater than 15:1, and web density is more than 1.10, preferably more than 1.20, especially more than 1.30 g/cm$^3$. Web length and thickness is determined under the microscope for example, and the density of the foam webs is determined according to the Archimedian principle, for example, by dipping the foams into a suitable liquid such as isopropanol, cf. EP-A-0 017 72.

In process step (b), the foam is conditioned at from 120° C. to 300° C. for from 1 to 180 minutes. It is heated to a temperature in the range from 120° C. to 260°, particularly preferably in the range from 150° C. to 250° C., for from preferably 3 minutes to 60 minutes, substantially removing water, blowing agent and formaldehyde and supplementarily curing the foam resin. This heat treatment may be carried out immediately following foam production in the same apparatus or in a downstream apparatus; but it can also be carried out at a later time regardless of the foaming process. Conditioned foams are substantially less prone to shrink and have a lower equilibrium moisture content than products which have not been conditioned. Formaldehyde emissions are similarly substantially reduced compared to the formaldehyde emissions of unconditioned products. Formaldehyde detachment is less than 100 mg of formaldehyde/kg of foam, preferably less than 20 mg formaldehyde/kg of foam (measured according to EU Standard ISO 14184-1).

The foams can be produced as sheets, blocks or webs up to 2 m in height or as foams a few mm in thickness, for example, in the range from 0.5 to 7 mm. The preferred foam height (in the foam rise direction) is in the range from 10 cm to 100 cm for 2.45 GHz microwaves. All desired sheet or fleece thicknesses can be cut out of such foam blocks.

To further reduce the formaldehyde emissions of the foams with or without increasing the absorption rate of the foams for water and body fluids, they are treated in process step (c), either during the conditioning or thereafter, with at least one polymer containing primary and/or secondary amino groups and having a molar mass of not less than 300. The treatment of the foam may be carried out even during the conditioning, for example, by having hot air flow through the melamine-formaldehyde resin foam to remove all volatiles and adding polymers containing primary and/or secondary amino groups to this conditioning air, for example, in the form of an aerosol. This makes it possible to lower the formaldehyde emissions of the foams with or without imparting a hydrophilic effect on them without the foams having to be subsequently subjected to a further treatment.

In process step (c), the foams are treated with at least one polymer containing primary and/or secondary amino groups and having a molar mass of not less than 300. A treatment of the surface of the foam may also be effected by applying crosslinked polymers or a crosslinked, hydrophilic sheath, for example, by first applying polymers containing primary and/or secondary amino groups to the surface of the foams, then adding a crosslinker thereon and reacting it with the functional groups of the polymers.

The polymeric treatments are normally applied in dissolved form by dissolving them in a solvent. They may also be applied in the form of aqueous dispersions or dispersions in an organic solvent to the melamine-formaldehyde resin foams. The treatment may be effected, for example, by dipping the melamine-formaldehyde foam body in the liquid which contains, in dissolved or in dispersed form, at least one polymer containing primary and/or secondary amino groups. Alternatively, the liquid comprising the dissolved or dispersed polymeric treatment may also be sprayed onto the foam surface. Thereafter, the solvent is removed from the thus treated foam body, for example, by drying the foam.

The amino-containing polymer reacts with the melamine-formaldehyde resin foam thus prepared and/or is adsorbed on the polymer surfaces. The amount of polymeric treatment added is apportioned in such a way that the formaldehyde emissions of the foam are reduced to such an extent that they amount to less than 100 mg of formaldehyde/kg of foam.

The mechanical properties of the foam (flexibility) should not be impaired by the modifying of the foam surface with the polymers. Preferably the polymeric treatment is added in such an amount that the resulting amount of polymer is in the range from 0.1 to 150% by weight, preferably from 0.5 to 90% by weight, especially in the range from 1 to 40% by weight, based on the foam.

Useful polymeric treatments include all cationic synthetic polymers containing primary and/or secondary amino and/or ammonium groups. Examples of such cationic polymers are vinylamine polymers, crosslinked polyamidoamines, ethyleneimine-grafted crosslinked polyamidoamines, polyethyleneimines, alkoxylated polyethyleneimines, crosslinked polyethyleneimines, amidated polyethyleneimines, alkylated polyethyleneimines, polyamines, amine-epichlorohydrin polycondensates, water-soluble polyaddition products of multifunctional epoxides and multifunctional amines, alkoxylated polyamines, polyallylamines and/or condensates of lysine, ornithine or arginine.

Vinylamine polymers (i.e., polymers containing vinylamine units) are preparable, for example, from open-chain N-vinylcarboxamides of the formula

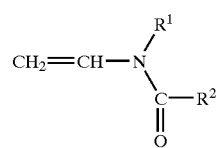

(I)

where $R^1$ and $R^2$ are identical or different and are each hydrogen or $C_1$- to $C_6$-alkyl. Useful monomers include, for example, N-vinylformamide ($R^1=R^2=H$ in formula I) N-vinyl-N-methylformamide, N-vinyl-acetamide, N-vinyl-N-methylacetamide, N-vinyl-N-ethylacetamide, N-vinyl-N-methylpropionamide and N-vinylpropionamide. To prepare the polymers, the monomers mentioned may be polymerized alone, mixed with each other or together with other monoethylenically unsaturated monomers. Homo- and copolymers of N-vinylformamide are preferred as starting material. Vinylamine polymers are known, for example, from U.S. Pat. No. 4,421,602, U.S. Pat. No. 5,334,287, EP-A-0 216 387 and EP-A-0 251 182. They are obtained by acid, base or enzymatic hydrolysis of polymers containing units derived from monomers of the formula I.

Useful monoethylenically unsaturated monomers for copolymerization with N-vinylcarboxamides include all compounds copolymerizable therewith. Examples thereof are vinyl esters of saturated carboxylic acids of from 1 to 6 carbon atoms such as the vinyl formate, vinyl acetate, vinyl propionate and vinyl butyrate and vinyl ethers such as $C_1$–$C_6$-alkyl vinyl ethers, e.g., methyl or ethyl vinyl ether. Useful comonomers further include ethylenically unsaturated $C_3$–$C_6$-carboxylic acids, for example, acrylic acid, methacrylic acid, maleic acid, crotonic acid, itaconic acid and vinylacetic acid and also their alkali metal and alkaline earth metal salts, esters, amides and nitriles of the carboxylic acids mentioned, for example, methyl acrylate, methyl methacrylate, ethyl acrylate and ethyl methacrylate.

Further useful carboxylic acids are derived from glycols or polyalkylene glycols where in each case only one OH group is esterified, for example, hydroxyethyl acrylate, hydroxyethyl methacrylate, hydroxypropyl acrylate, hydroxybutyl acrylate, hydroxypropyl methacrylate, hydroxybutyl methacrylate and also monoacrylate esters of polyalkylene glycols having a molar mass of from 500 to 10,000. Useful comonomers further include esters of ethylenically unsaturated carboxylic acids with aminoalcohols, for example, dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, diethylaminopropyl acrylate, dimethylaminobutyl acrylate and diethylaminobutyl acrylate. Basic acrylates can be used in the form of the free bases, the salts with mineral acids such as hydrochloric acid, sulfuric acid or nitric acid, the salts with organic acids such as formic acid, acetic acid, propionic acid or sulfonic acids or in quaternized form. Useful quaternizing agents include, for example, dimethyl sulfate, diethyl sulfate, methyl chloride, ethyl chloride or benzyl chloride.

Useful comonomers further include amides of ethylenically unsaturated carboxylic acids such as acrylamide, methacrylamide and also N-alkylmonoamides and diamides of monoethylenically unsaturated carboxylic acids with alkyl radicals of from 1 to 6 carbon atoms, for example, N-methylacrylamide, N,N-dimethylacrylamide, N-methylmethacrylamide, N-ethyl-acrylamide and N-propylacrylamide and tert-butylacrylamide and also basic (meth)acrylamides, for example, dimethylaminoethylacrylamide, dimethylaminoethylmethacrylamide, diethylaminoethylacrylamide, diethylaminoethylmethacrylamide, dimethylaminopropylacrylamide, diethylaminopropylacrylamide, dimethylaminopropylmethacrylamide and diethylaminopropylmethacrylamide.

Useful comonomers further include N-vinyl-pyrrolidone, N-vinylcaprolactam, acrylonitrile., methacrylonitrile, N-vinylimidazole and also substituted N-vinylimidazoles, for example, N-vinyl-2-methylimidazole, N-vinyl-4-methylimidazole, N-vinyl-5-methylimidazole, N-vinyl-2-ethylimidazole and N-vinylimidazolines such as N-vinylimidazoline, N-vinyl-2-methylimidazoline and N-vinyl-2-ethylimidazoline. N-vinylimidazoles and N-vinylimidazolines are used not only in the form of the free bases but also after neutralization with mineral acids or organic acids or after quaternization, a quaternization being preferably effected with dimethyl sulfate, diethyl sulfate, methyl chloride or benzyl chloride. Also useful are diallyl-dialkylammonium halides, for example, diallyldimethylammonium chlorides.

Useful comonomers further include sulfo-containing monomers, for example, vinylsulfonic acid, allylsulfonic acid, methallylsulfonic acid, styrenesulfonic acid, the alkali metal or ammonium salts of these acids or 3-sulfopropyl acrylate. Since the amphoteric copolymers contain more cationic units than anionic units, they have a cationic charge overall.

The copolymers contain for example
from 99.99 to 1 mol %, preferably from 99.9 to 5 mol %, of N-vinylcarboxamides of the formula I and
from 0.01 to 99 mol %, preferably from 0.1 to 95 mol %, of other monoethylenically unsaturated monomers copolymerizable therewith in copolymerized form.

To prepare vinylamine polymers it is preferable to start from homopolymers of N-vinylformamide or from copolymers obtainable by copolymerization of
N-vinylformamide with
vinyl formate, vinyl acetate, vinyl propionate, acrylonitrile, N-vinylcaprolactam, N-vinylurea, acrylic acid, N-vinylpyrrolidone or $C_1$- to $C_6$-alkyl vinyl ethers and subsequent hydrolysis of the homo or copolymers to form vinylamine units from the copolymerized N-vinylformamide units, the degree of hydrolysis being, for example, in the range from 0.1 to 100 mol %.

The hydrolysis of the above-described polymers is effected according to known processes by the action of acids, bases or enzymes. This converts the copolymerized monomers of the above-indicated formula I through detachment of the group

where $R^2$ is as defined in the formula I, into polymers which contain vinylamine units of the formula

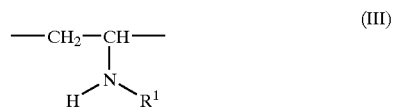

where $R^1$ is as defined in the formula I. When acids are used as hydrolyzing agents, the units III are present as ammonium salt.

The homopolymers of the N-vinylcarboxamides of the formula I and their copolymers may be hydrolyzed to an extent in the range from 0.1 to 100 mol %, preferably to an extent in the range from 70 to 100 mol %. In most cases, the degree of hydrolysis of the homo- and copolymers is in the range from 5 to 95 mol %. The degree of hydrolysis of the homopolymers is synonymous with the vinylamine units content of the polymers. In the case of copolymers containing units derived from vinyl esters, the hydrolysis of the N-vinylformamide units can be accompanied by a hydrolysis of the ester groups with the formation of vinyl alcohol units. This is the case especially when the hydrolysis of the copolymers is carried out in the presence of aqueous sodium hydroxide solution. Copolymerized acrylonitrile is likewise chemically modified in the hydrolysis, for example, into amide groups or carboxyl groups. The homo- and copolymers containing vinylamine units may optionally contain up to 20 mol % of amidine units, formed, for example, by reaction of formic acid with two adjacent amino groups or by intramolecular reaction of an amino group with an adjacent amide group, for example, of copolymerized N-vinylformamide. The molar masses of vinylamine polymers range, for example, from 500 to 10 million, preferably from 1,000 to 5 million (determined by light scattering). This molar mass range corresponds, for example, to K values of from 5 to 300, preferably from 10 to 250 (determined by the method of H. Fikentscher in 5% aqueous sodium chloride solution at 25° C. and a polymer concentration of 0.5% by weight).

The vinylamine polymers are preferably used in salt-free form. Salt-free aqueous solutions of vinylamine polymers are preparable, for example, from the above-described salt-containing polymer solutions by means of ultrafiltration using suitable membranes having molecular weight cutoffs at, for example, from 1,000 to 500,000 daltons, preferably from 10,000 to 300,000 daltons. The hereinbelow described aqueous solutions of other polymers containing amino and/or ammonium groups are likewise obtainable in salt-free form by means of ultrafiltration.

Polyethyleneimines are prepared, for example, by polymerizing ethyleneimine in an aqueous solution in the presence of acid-detaching compounds, acids or Lewis acids as catalyst. Polyethyleneimines have, for example, molar masses of up to 2 million, preferably of from 200 to 1,000,000. Particular preference is given to using polyethyleneimines having molar masses of from 500 to 750,000. Useful polyethyleneimines further include water-soluble crosslinked polyethyleneimines which are obtainable by reaction of polyethyleneimines with crosslinkers such as epichlorohydrin or bischlorohydrin ethers of polyalkylene glycols containing from 2 to 100 ethylene oxide and/or propylene oxide units and which still contain free primary and/or secondary amino groups. Also useful are amidic polyethyleneimines which are obtainable, for example, by amidation of polyethyleneimines with $C_1$- to $C_{22}$- monocarboxylic acids. Useful cationic polymers further include alkylated polyethyleneimines and alkoxylated polyethyleneimines. Alkoxylation is carried out using, for example, from 1 to 5 ethylene oxide or propylene oxide units per NH unit in the polyethyleneimine.

Useful polymers containing primary and/or secondary amino and/or ammonium groups also include polyamidoamines, which are preparable, for example, by condensing dicarboxylic acids with polyamines. Useful polyamidoamines are obtained, for example, when dicarboxylic acids having from 4 to 10 carbon atoms are reacted with polyalkylene polyamines containing from 3 to 10 basic nitrogen atoms in the molecule. Useful dicarboxylic acids include, for example, succinic acid, maleic acid, adipic acid, glutaric acid, suberic acid, sebacic acid or terephthalic acid. Polyamidoamines may also be prepared using mixtures of dicarboxylic acids as well as mixtures of plural polyalkylenepolyamines. Useful polyalkylenepolyamines include, for example, diethylenetriamine, triethylenetetramine, tetraethylenepentamine, dipropylenetriamine, tripropylenetetramine, dihexamethylenetriamine, aminopropyl-ethylenediamine and bisaminopropylethylenediamine. The dicarboxylic acids and polyalkylenepolyamines are heated at an elevated temperature, for example, at from 120° C. to 220° C., preferably at from 130° C. to 180° C., to prepare polyamidoamines. The water of condensation formed is removed from the system. The condensation may also employ lactones or lactams of carboxylic acids having from 4 to 8 carbon atoms. The amount of a polyalkylenepolyamine used per mole of a dicarboxylic acid is, for example, in the range from 0.8 to 1.4 mol.

Amino-containing polymers further include ethyleneimine-grafted polyamidoamines. They are obtainable from the above-described polyamidoamines by a reaction with ethyleneimine in the presence of acids or Lewis acids such as sulfuric acid or boron trifluoride etherates at, for example, from 80° C. to 100° C. Compounds of this kind are described, for example, in DE-B-24 34 816.

Useful cationic polymers also include crosslinked or uncrosslinked polyamidoamines which may additionally have been grafted with ethyleneimine prior to crosslinking. Crosslinked ethyleneimine-grafted polyimidoamines are water-soluble and have, for example, an average molecular weight of from 3,000 to 2 million Daltons. Customary crosslinkers include, for example, epichlorohydrin or bischlorohydrin ethers of alkylene glycols and polyalkylene glycols.

Useful polymers having primary and/or secondary amino and/or ammonium groups also include polyallylamines. Polymers of this kind are obtained by homopolymerization of allylamine, preferably in acid-neutralized form, or by copolymerizing allylamines with other monoethylenically unsaturated monomers described above as comonomers for N-vinylcarboxamides The above-mentioned cationic polymers have, for example, K values of from 8 to 300, preferably from 15 to 180 (determined by the method of H. Fikentscher in 5% aqueous sodium chloride solution at 25° C. and a polymer concentration of 0.5% by weight). At pH 4.5, for example, they have a charge density of at least 1, preferably at least 4, meq/g of polyelectrolyte.

Preferred cationic polymers are polyethyleneimine, polymers containing vinylamine units, polymers containing lysine units or mixtures thereof. Examples of preferred cationic polymers are:

polylysines of $M_w$ 250–250,000, preferably 500–100,000, and also lysine condensates having $M_w$ molar masses of from 250 to 250,000, the cocondensable component being selected, for example, from amines, polyamines, ketene dimers, lactams, alcohols, alkoxylated amines, alkoxylated alcohols and/or nonproteinogenic amino acids, vinylamine homopolymers, 1–99% hydrolyzed polyvinylformamides, copolymers of vinylformamide and vinyl acetate, vinyl alcohol, vinylpyrrolidone or acrylamide, each having molar masses of 3,000 2,000,000, polyethyleneimines, cross linked polyethyleneimines or amidated polyethyleneimines which each have molar masses of from 500 to 3,000,000.

Polymers containing primary and/or secondary amino groups and having been contacted with the melamine-formaldehyde resin foams to reduce formaldehyde omissions with or without imparting hydrophilicity may optionally be crosslinked thereon. Crosslinking of the foams treated with polymers containing primary and/or secondary amino groups is obtained, for example, by reaction with at least bifunctional crosslinkers such as epichlorohydrin, bischlorohydrin ethers of polyalkylene glycols, polyepoxides, multifunctional esters, multifunctional acids such as polycarboxylic acids, for example, oxalic acid, succinic acid, adipic acid, tartaric acid, citric acid, polyacrylic acid, polymethacrylic acid, polyacrylamidomethylpropanesulfonic acid, copolymers of acrylic acid and maleic acid, sulfuric acid, phosphoric acid, acrylic acid, methacrylic acid, maleic acid, maleic anhydride, itaconic acid or multifunctional (meth)acrylates such as methylenebisacrylamide, ethylene glycol diacrylate, ethylene glycol dimethacrylate, polyethylene glycol diacrylates or dimethacrylates having a number average molecular weight of from 200 to 4,000, diacrylates or dimethacrylates of addition products of from 2 to 400 mol of ethylene oxide onto 1 mol of a diol having at least 3 carbon atoms in the molecule. It is further possible to use:

acrylic acid, methacrylic acid, maleic acid, maleic anhydride or esters of at least bifunctional carboxylic acids, for example, dialkyl oxalates, dialkyl maleates, dialkyl fumarates, dialkyl succinates and dialkyl malonates.

The hydrophilic open-celled resilient melamine-formaldehyde resin foams prepared by the process of the invention emit less than 100 mg of formaldehyde per kg of foam when measured under the conditions of the EU standard EN ISO 14184-1. These foams usually emit less than 20 mg of formaldehyde per kg of foam under the measuring conditions mentioned.

The inventive foams based on melamine-formaldehyde resins are used in hygiene articles to acquire, distribute and immobilize body fluids, especially blood. Their hydrophilic character provides spontaneous acquisition of aqueous body fluids. The open-celled structure ensures rapid transportation into the foam interior. Hygiene articles which include the foams to be used according to the invention are essentially infant diapers, incontinence products, femcare articles, wound contact materials or secondary wound dressings.

The melamine-formaldehyde resin foams for inventive use in the hygiene sector are open-celled and hydrophilic. The droplet absorption rate of the melamine-formaldehyde foams according to the invention is less than 5 seconds, preferably less than 2 seconds, particularly preferably less than 1 second.

The open-celled resilient foams are preferably incorporated as sheet-like structures in the form of foam fleeces from 0.1 to 10 mm, preferably from 1 to 5 mm, in thickness into hygiene products such as infant diapers, incontinence and femcare articles or as wound contact materials or in dressing materials. Foam density is, for example, in the range from 5 to 200 g/l, preferably from 10 to 50 g/l. The foams preferably have a webbed structure, a BET specific surface area of more than 0.5 $m^2$/g, for example, in the range from 1 to 7 $m^2$/g, a Free Swell Capacity of more than 20 g/g, for example, from 80 to 120 g/g, and a tensile strength of >60 $J/m^2$, for example, from 100 to 600 $J/m^2$, in the wet state.

A hygiene article generally constitutes a combination of a liquid-impervious backsheet, a liquid-pervious topsheet, and an absorbent interlayer core. Hygiene articles of this type are known and described, for example, in DE-U-92 18 991 and EP-A-0 689 818. The absorbent composition is fixed between topsheet and backsheet. Elastic cuffs and self-adhesive tabs may optionally be integrated in the hygiene article. A preferred hygiene article construction is known, for example, from U.S. Pat. No. 3,860,003.

When the hydrophilic open-celled resilient foams are used in a hygiene article, there are, for example, two ways of configuring the absorbent interlayer core:

1. The melamine-formaldehyde foam layer is used as the absorbent interlayer core without further layers. It then acts simultaneously as acquisition or acquisition/distribution layer and as storage layer.

2. The absorbent interlayer core consists of (a) a melamine-formaldehyde foam layer, which acts as acquisition or acquisition/distribution layer, and (b) a storage layer containing 10–100% by weight of highly swellable hydrogel.

The storage layer either is a hydrogel layer or constitutes compositions which include highly swellable hydrogels or are fixed to them. Any composition is suitable that is capable of accommodating highly swellable hydrogels and also being integrated into the absorbent core. A multiplicity of such compositions is already known and described in detail in the literature. A composition for installing the highly swellable hydrogels can be, for example, a fiber matrix consisting of a cellulose fiber mixture (airlaid web, wet laid web) or of synthetic polymer fibers (meltblown web, spunbonded web), or else of a fiber blend of cellulose fibers and synthetic fibers. Furthermore, open-celled foams or the like may be used to install highly swellable hydrogels.

Alternatively, such a composition can be the result of fusing two individual layers to form one or, better, a multiplicity of chambers which contain the highly swellable hydrogels. In this case, at least one of the two layers should be water-pervious. The second layer may be either water-pervious or water-impervious. The layer material used may be tissues or other fabrics, closed or open-celled foams, perforated films, elastomers or fabrics composed of fiber material. When the storage layer consists of a composition of layers, the layer material should have a pore structure whose pore dimensions are small enough to retain the highly swellable hydrogel particles. The above examples on the composition of the storage layer also include laminates composed of at least two layers between which the highly swellable hydrogels can be installed and fixed.

Furthermore, the storage layer can consist of a carrier material, for example, a polymer film, on which the highly swellable hydrogel particles are fixed. The fixing can be effected not only on one side but also on both sides. The carrier material can be water-pervious or water-impervious.

Into the above compositions of the storage layer, the highly swellable hydrogels may be installed with a weight fraction of from 10 to 100% by weight, preferably from 40 to 100% by weight and particularly preferably from 70 to 100% by weight. When the above storage layer composition constitutes a fiber matrix, then the absorbent composition results from a mixture of fiber materials and highly swellable hydrogels.

The storage layer may contain manifold fiber materials, which are used as fiber network or matrices. The present invention encompasses not only fibers of natural origin (modified or unmodified) but also synthetic fibers.

Examples of cellulose fibers include cellulose fibers which are customarily used in absorption products, such as fluff pulp and pulp of the cotton type. The materials (hard- or softwoods), production processes, such as chemical pulp, semi-chemical pulp, chemothermomechanical pulp (CTMP) and bleaching processes are not particularly restricted. For example, natural cellulose fibers such as cotton, flax, silk, wool, jute, ethylcellulose and cellulose acetate are used.

Suitable synthetic fibers are produced from polyvinyl chloride, polyvinyl flouride, polytetraflouroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/-polypropylene, polyethylene/polyester, polypropylene/polyester, copolyester/polyester, polyamide fibers (Nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent core, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any desired fiber from 1 to 200 mm in length and from 0.1 to 100 denier (gram per 9000 meters) in diameter is preferred. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10,000 meters) is particularly preferred. The form of the fiber is not particularly restricted and examples include woven types, narrow cylindrical types, cut/chopped yarn types, staple fiber types and continuous filament fiber types.

The fibers in the absorbent composition of the invention can be hydrophilic, hydrophobic or a combination of the two. According to the definition of Robert F. Gould in the 1964 American Chemical Society publication "Contact angle, wetability and adhesion," a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the highly swellable hydrogels. In the manufacturing process, layers having different hydrophilicities are used to create a gradient which channels impinging fluid to the hydrogel, where it is ultimately absorbed.

Suitable hydrophilic fibers for use in the absorbent interlayer core of the invention include, for example, cellulosic fibers, modified cellulose fibers, rayon, polyester fibers, for example, polyethylene terephthalate (DACRON®), and hydrophilic nylon (HYDROFIL®). Suitable hydrophilic fibers may also be obtained by hydrophilicizing hydrophobic fibers, for example, the treatment of thermoplastic fibers obtained from polyolefins (e.g., polyethylene or polypropylene, polyamides, polystyrenes, polyurethanes, etc.) with surfactants or silica. However, for cost reasons and ease of availability, cellulosic fibers are preferred.

The highly swellable hydrogel particles are embedded into the fiber material described. This can be done in various ways, for example, by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -transporting fiber matrix may comprise synthetic fiber or cellulosic fiber or a mixture of synthetic fiber and cellulosic fiber, in which case the mixing ratio may vary from (100 to 0) synthetic fiber:(0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include, for example, polyamide-epichlorohydrin coatings (KYMENE® 557H), polyacrylamide coatings (described in U.S. Pat. No. 3,556,932 or as the PAREZ® 631 NC commercial product), melamine-formaldehyde coatings and polyethyleneimine coatings.

Cellulosic fibers may also be chemically stiffened by chemical reaction. For instance, suitable crosslinker substances may be added to effect crosslinking, taking place within the fiber. Suitable crosslinker substances are typical substances used for crosslinking monomers. Included but not limited thereto are $C_2$–$C_8$-dialdehydes, $C_2$–$C_8$-monoaldehydes having acid functionality and in particular $C_2$–$C_9$-polycarboxylic acids. Specific substances from this series are, for example, glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known, cf., for example, WO-A-91/11162. The chemical crosslinking imparts stiffening to the fiber material, which is ultimately reflected in improved dimensional stability for the hygiene article as a whole. The individual layers from which the hygiene article is constructed are joined together by methods known to one skilled in the art, for example, by fusion by heat treatment, addition of hot-melt adhesives, latex binders, etc.

Generally, the invention utilizes a hydrophilicized fleece of an open-celled resilient melamine-formaldehyde resin foam having very low formaldehyde emissions as or in the absorbent interlayer core. The dimensions (thickness) of the absorbent interlayer when used as an absorbent core is generally in the range from 0.5 to 10 mm, preferably in the range from 1 to 5 mm. When used as an acquisition and distribution layer in combination with a storage layer, the thickness is in the range from 0.1 to 10 mm, preferably in the range from 0.5 to 3 mm.

The topsheet can be produced in various ways, for example, as a woven, nonwoven, spun or combed fiber mixture. Preference is given to using a combed fiber mixture which is thermally bonded to form the topsheet. The basis weight of the topsheet is preferably in the range from 18 to 25 g/m². It has a tensile strength of at least 400 g/cm in the dry state and 55 g/cm in the wet state.

The backsheet is usually a liquid-impervious material, for example, polyolefins (a polyethylene backsheet for example) to protect the user's clothing from possible leakage.

The individual layers from which the hygiene articles are constructed are joined together by known methods, for example, by intermelting the layers by heat treatment, addition of hot-melt adhesives, latex binders, etc. The absorbent interlayer core is positioned between topsheet and backsheet.

Methods of Measurement

Droplet Absorption Rate

A single droplet of a 0.9% sodium chloride solution is pipetted onto a foam layer about 5 mm in thickness and the time taken for the droplet to disappear into the foam. The foam was rated hydrophilic when the absorption time was <5 sec.

Density

Any suitable gravimetric method can be used for determining the density of the foam. What is determined is the mass of solid foam per unit volume of foam structure. A method for density determination of the foam is described in ASTM Method No. D 3574-86, Test A. This method was originally developed for the density determination of urethane foams, but can also be used for this purpose. By this method, the dry mass and volume of a preconditioned sample is determined at 22° C. ±2° C. Volume determinations of larger sample dimensions are carried out under atmospheric pressure.

Free Swell Capacity (FSC)

This method is used to determine the free swellability of the open-celled resilient melamine-formaldehyde foam. To determine FSC, a test piece of suitable size, for example, with an area of 1 cm×1 cm is cut out of a foam blank and weighed. The test piece is placed in an excess of test solution (at least 0.83 l of sodium chloride solution/1 g of foam) for 30 minutes and then removed. The test piece is subsequently allowed to drip for 10 minutes before it is hung up by one corner to avoid compression. The amount of liquid is determined by weighing the test piece.

The test solution used was a 0.9% by weight aqueous NaCl solution.

Acquisition Time

The open-celled resilient melamine-formaldehyde foam was cut into layers 1.5 or 2 mm or 4 mm in thickness to determine the acquisition time. A commercially available diaper was carefully cut open, the high loft used as acquisition medium removed and instead the open-celled resilient melamine-formaldehyde foam layer inserted. The diaper was resealed. Synthetic urine solution was applied to it through a plastic plate having a ring in the middle (inner diameter of the ring 6.0 cm, height 4.0 cm). The plate was loaded with additional weights so that the total weight on the diaper was 13.6 g/cm². The plastic plate was placed on the diaper in such a way that the center of the diaper was also the center of the application ring. 60 ml of 0.9% by weight sodium chloride solution were applied three times. The sodium chloride solution was measured in a graduated cylinder and applied to the diaper in a continuous stream through the ring in the plate. At the same time the time was taken for the solution to penetrate completely into the diaper. The time measured was noted as acquisition time 1. Thereafter, the diaper was loaded with a plate for 20 min, the load being maintained at 13.6 g/cm². This was followed by the second application of the liquid. The time measured was noted as acquisition time 2. The same method was employed to determine acquisition time 3.

Specific Surface Area

Specific surface area was determined by the BET method as set forth in DIN 66 132.

Formald Hyde Emission

Determined by Edana method 210.1-99 (testing to EU Standard EN ISO 14184-1)

One g of the foam sample to be tested is cut into small pieces, introduced into an Erlenmeyer flask together with 100 ml of water and tightly sealed. The Erlenmeyer flask is placed into a water bath maintained at 40° C. and is left therein for 60 min with periodic shaking. Subsequently, the solution obtained is filtered off or the foam is expressed. The formaldehyde content of the solution obtained is determined by the acetylacetone method.

Unless the context suggests otherwise, the percentages in the examples are by weight. The molar masses M of the polymers were determined by light scattering. The K values of the polymers were determined by the method of H. Fikentscher, Cellulose-Chemie 13 (1932), 58–64, 71–74 at 25° C. and the particular concentrations, pH values and solvents reported for the individual polymers in Table 1:

TABLE 1

| Polymer | Solvent | Concentration of solution [% by weight] | pH of solution |
| --- | --- | --- | --- |
| Polyvinylamine | 3% aqueous NaCl solution | 0.5 | 11.0 |
| Polyacrylic acid | Water | 1.0 | 7.0 (neutralized with NaOH) |
| Polylysine | Water | 1.0 | 10.3 |

EXAMPLES

Comparative Example 1

Seventy-five parts of a spray-dried melamine-formaldehyde precondensate (molar ratio 1:3) were dissolved in 25 parts of water. This resin solution was admixed with 3% of formic acid, 2% of a sodium $C_{12}/C_{18}$-alkanesulfonate and 19% of pentane, each based on the resin. The mixture was vigorously stirred and subsequently foamed in a polypropylene foaming mold by irradiation with microwave energy at 2.54 GHz. The foam was dried at 100° C. and subsequently conditioned at 220° C. for 30 min. The melamine-formaldehyde foam thus prepared was hydrophilic and had a density of 10 g/l. Formaldehyde emissions after 1 h of storage in water at 40° C. were 150 mg of formaldehyde/kg of foam. The Free Swell Capacity was 103 g/g. The foam had a BET specific surface area of 5.3 $m^2/g$.

Comparative Example 2

Seventy parts of a spray-dried melamine-formaldehyde precondensate (molar ratio 1:1.6) were dissolved in 30 parts of water. This resin solution was admixed with 3% of an emulsifier mixture of an alkanolamide and ethoxylated fatty alcohol and also with 3% of formic acid and 10% of pentane. The mixture was foamed, and the foam dried and conditioned, as described in Comparative Example 1. The foam thus prepared was hydrophobic and its density was likewise 10 g/l. Formaldehyde emissions were less than 20 mg of formaldehyde/kg of foam.

Inventive Example 1

The foam prepared according to Comparative Example 1 was cut into layers about 3 mm in thickness, coated with 1.6% of polyvinylamine (K value 90) by spraying with an aqueous solution of polyvinylamine and subsequently dried at 85° C. under reduced pressure. The formaldehyde emission of the foam thus obtained was then measured. The results are reported in Table 2.

Inventive Example 2

The foam prepared according to Comparative Example 1 was cut into layers about 3 mm in thickness, coated with 3.2% of polyvinylamine (K value 90) by spraying with an aqueous solution of polyvinylamine and subsequently dried at 85° C. under reduced pressure. The formaldehyde emission of the foam thus obtained was then measured. The results are reported in Table 2.

Inventive Example 3

The foam prepared according to Comparative Example 1 was cut into layers about 3 mm in thickness, coated with polyvinylamine (K value 105) by dipping into a 1% aqueous polyvinylamine solution and subsequently dried at 150° C. under reduced pressure. The formaldehyde emission of the foam thus obtained was then measured. The results are reported in Table 2.

Inventive Example 4

The foam prepared according to Comparative Example 1 was cut into layers about 3 mm in thickness, coated with 3.2% of a mixture of polyvinylamine and ethylene glycol bisglycidyl ether in a ratio of 40:1 by spraying with an aqueous solution thereof (based on the solids content of the mixture) and subsequently dried at 85° C. under reduced pressure. The formaldehyde emission of the foam thus obtained was then measured. The results are reported in Table 2.

Inventive Example 5

The foam prepared according to Comparative Example 1 was cut into layers about 3 mm in thickness, coated with 50 mol % HCl-neutralized polyvinylamine (K value 90) by spraying with an aqueous solution of polyvinylamine and subsequently dried at 85° C. under reduced pressure. The formaldehyde emission of the foam thus obtained was then measured. The results are reported in Table 2.

Inventive Example 6

The foam prepared according to Comparative Example 1 was cut into layers about 3 mm in thickness, coated with polylysine (K value 17) by dipping into a 1% aqueous polylysine solution and subsequently dried at 150° C. under reduced pressure. The formaldehyde emission of the foam thus obtained was then measured. The results are reported in Table 2.

TABLE 2

| Example No. | Coating | Amount of formaldehyde released [ppm] |
| --- | --- | --- |
| Comparative 1 | — | 150 |
| Inventive 1 | 1.6% of polyvinylamine K 90 | 25 |
| Inventive 2 | 3.2% of polyvinylamine K 90 | 14 |
| Inventive 3 | polyvinylamine K 105 | <10 |
| Inventive 4 | 3.2% of reaction mixture of 40:1 polyvinylamine K 90 and ethylene glycol diglycidyl ether | 28 |
| Inventive 5 | 3.2% of polyvinylamine K 90 50 mol % neutralized with HCl | 21 |
| Inventive 6 | polylysine, K 17 | 15 |

Inventive Example 7

The foam prepared according to Comparative Example 2 was cut into layers about 3 mm in thickness, coated with 6.4% of polyvinylamine (K value 90) by spraying with an aqueous solution of polyvinylamine and subsequently dried at 150° C. under reduced pressure. The formaldehyde emission of the foam thus obtained was then measured. The results are reported in Table 3.

Inventive Example 8

The foam prepared according to Comparative Example 2 was cut into layers about 3 mm in thickness, coated with 6.4% of polyvinylamine (K value 105) by spraying with an aqueous solution of polyvinylamine and subsequently dried at 150° C. under reduced pressure. The formaldehyde emission of the foam thus obtained was then measured. The results are reported in Table 3.

Inventive Example 9

The foam prepared according to Comparative Example 2 was cut into layers about 3 mm in thickness, coated with polylysine (K value 17) by dipping into a 1% aqueous polylysine solution and subsequently dried at 150° C. under reduced pressure. The formaldehyde emission of the foam thus obtained was then measured. The results are reported in Table 3.

Inventive Example 10

The foam prepared according to Comparative Example 2 was cut into layers about 3 mm in thickness, coated with polyethyleneimine (molar mass M 25,000) by dipping into a 1% aqueous polyethyleneimine solution and subsequently dried at 85° C. under reduced pressure. The formaldehyde emission of the foam thus obtained was then measured. The results are reported in Table 3.

Inventive Example 11

The foam prepared according to Comparative Example 2 was cut into layers about 3 mm in thickness, coated with 3.2% of a mixture of polyvinylamine and ethylene glycol bisglycidyl ether in a ratio of 40:1 by spraying with an aqueous solution thereof (based on the solids content of the mixture) and subsequently dried at 85° C. under reduced pressure. The formaldehyde emission of the foam thus obtained was then measured. The results are reported in Table 3.

Inventive Example 12

The foam prepared according to Comparative Example 2 was cut into layers about 3 mm in thickness, coated with polyvinylamine (K value 90) by dipping into a 1% aqueous polyvinylamine solution and subsequently dried at 150° C. under reduced pressure. Subsequently the thus treated foam sample was coated with 4% polyacrylic acid (K value 110) by spraying with an aqueous solution of polyacrylic acid and dried at 85° C. under reduced pressure. The formaldehyde emission of the foam thus obtained was then measured. The results are reported in Table 3.

TABLE 3

| Example | Coating | Amount of formaldehyde released [ppm] | Hydrophilic | Hydrophobic |
|---|---|---|---|---|
| Comparative 2 | — | 15 | | X |
| Inventive 7 | polyvinylamine, K 90 | <5 | X | |
| Inventive 8 | 6.4% of polyvinylamine, K 105 | <5 | X | |
| Inventive 9 | polylysine, K 17 | <5 | X | |
| Inventive 10 | polyethylene-imine, MW 25,000 | <5 | X | |
| Inventive 11 | 3.2% of reaction mixture of 40:1 of polyvinylamine (K 90)/ethylene glycol diglycidyl ether | <5 | X | |
| Inventive 12 | polyvinylamine, K 90 and subsequently polyacrylic acid K 110 | <5 | X | |

The data shown in Table 3 reveal that coating the foams with primary and/or secondary polyamines ensures the necessary hydrophilicity and may also further reduce formaldehyde emissions.

Inventive Example 13

The melamine-formaldehyde resin foam treated according to Inventive Example 8 was cut into layers 2 mm in thickness. A commercially available diaper was carefully cut open, the high loft removed and instead the 2 mm thick foam layer inserted into the diaper. The diaper was then resealed and the times were taken to absorb 3 successive additions of 60 ml of synthetic urine (0.9% aqueous sodium chloride solution). The measured values are reported in Table 4.

Inventive Example 14

Inventive Example 13 was repeated except that a foam prepared according to Inventive Example 9 was cut into layers 2 mm in thickness which were incorporated into a diaper. The measured values are reported in Table 4.

Comparative Example 3

A commercially available diaper was carefully cut open, the high loft removed, and then reinserted and the diaper resealed. This procedure is intended to ensure optimum comparability. The acquisition times were then determined. They are reported in Table 4.

Comparative Example 4

The low-formaldehyde foam of melamine-formaldehyde condensate prepared according to Comparative Example 2 was incorporated into a diaper as described in Inventive Example 13. The acquisition times were then determined for the absorption of synthetic urine. They are reported in Table 4.

Comparative Example 5

The low-formaldehyde foam of melamine-formaldehyde condensate prepared according to Comparative Example 1 was incorporated into a diaper as described in Inventive Example 13. The acquisition times were then determined for the absorption of synthetic urine. They are reported in Table 4.

TABLE 4

| Diaper | Time to absorb first 60 ml [sec] | Time to absorb second 60 ml [sec] | Time to absorb third 60 ml [sec] |
|---|---|---|---|
| Comparative Example 3 | 7 | 19 | 29 |
| Comparative Example 4 | 80 | 125 | 148 |
| Comparative Example 5 | 3 | 6 | 8 |
| Inventive Example 13 | 4 | 6 | 9 |
| Inventive Example 14 | 3 | 5 | 8 |

Table 4 reveals that the acquisition times of the low-formaldehyde foam coated with polymers containing primary and/or secondary amino groups are significantly better than those of a commercially available diaper and equivalent to those of the foam of Comparative Example 1.

What is claimed is:

1. Hydrophilic open-celled resilient foams comprising a melamine-formaldehyde resin prepared by
   (a) heating and crosslinking an aqueous solution or dispersion comprising a melamine-formaldehyde precondensate, an emulsifier, a blowing agent and a curing agent to form a foam,
   (b) then conditioning the foam at from 120° to 300° C. for from 1 to 180 minutes to remove volatiles, and
   (d) treating the foam during the conditioning or thereafter with at least one polymer containing primary and/or secondary amino groups and/or ammonium groups and having a molar mass of not less than 300.

2. The hydrophilic open-celled resilient foams as claimed in claim 1, wherein the melamine-formaldehyde precondensate has a molar ratio of melamine to formaldehyde in the range from 1:1.0 to 1:5.0.

3. The hydrophilic open-celled resilient foams as claimed in claim 1 or 2, wherein the melamine-formaldehyde precondensate has a molar ratio of melamine to formaldehyde in the range from 1:2.0 to 1:5.0.

4. The hydrophilic open-celled resilient foams as claimed in claim 1, wherein the melamine-formaldehyde precondensate has a molar ratio of melamine to formaldehyde in the range from 1:2.5 to 1:3.5.

5. The hydrophilic open-celled resilient foams as claimed in claim 1, wherein the polymer containing primary and/or secondary amino and/or ammonium groups has a molar mass of from 500 to 5 million.

6. The hydrophilic open-celled resilient foams as claimed in claim 5, wherein the molar mass of the polymer is in the range from 1,000 to 100,000.

7. The hydrophilic open-celled resilient foams as claimed in claim 1, wherein the polymer comprises vinylamine polymers, polyethyleneimines, lysine condensates, polyallylamines, or mixtures thereof.

8. A process for preparing hydrophilic open-celled resilient foams comprising melamine-formaldehyde resins, which comprises
   (a) heating and crosslinking an aqueous solution or dispersion comprising a melamine-formaldehyde precondensate, an emulsifier, a blowing agent and a curing agent to form a foam,
   (b) then conditioning the foam at from 120° to 300° C. for from 1 to 180 minutes to remove volatiles, and
   (c) treating the foam during the conditioning or thereafter with at least one polymer containing primary and/or secondary amino groups and/or ammonium groups and having a molar mass of not less than 300.

9. The process as claimed in claim 8, wherein the melamine-formaldehyde precondensate has a molar ratio of melamine to formaldehyde in the range from 1:2.0 to 1:5.0.

10. The process as claimed in claim 8 or 9, wherein the melamine-formaldehyde precondensate has a molar ratio of melamine to formaldehyde in the range from 1:2.5 to 1:3.5.

11. The process as claimed in claim 8, wherein the polymer comprises vinylamine polymers, polyethyleneimines, lysine condensates, polyallylamines, and mixtures thereof.

12. The process as claimed in claim 8, wherein the polymer has a molar mass of from 500 to 5 million.

13. The process as claimed in claim 8, wherein the polymer has a molar mass of from 1000 to 100,000.

14. The process as claimed in claim 8, wherein the polymer contains vinylamine units.

15. The process as claimed in claim 8, wherein the polymer comprises a polyethyleneimine.

16. A method of acquiring, distributing, and immobilizing body fluids comprising contacting the body fluid with a hydrophilic open-celled resilient foam of claim 1.

17. A hygiene article to acquire, distribute, and immobilize body fluids comprising a hydrophilic open-celled resilient foam of claim 1.

18. The article of claim 17, wherein the article is selected from the group consisting of infant diapers, incontinence products, femcare articles, wound contact materials and secondary wound dressings.

* * * * *